US009861299B1

(12) United States Patent
Jones et al.

(10) Patent No.: US 9,861,299 B1
(45) Date of Patent: Jan. 9, 2018

(54) SPIROMETRY-BASED PERSONAL HEALTH RISK ASSESSMENT DEVICE

(75) Inventors: William Jones, Chicago, IL (US); Scott Jones, Chicago, IL (US); Louis J. Heeb, St. Charles, MO (US)

(73) Assignee: Jones Medical Instrument Company, Oak Brook, IL (US)

( * ) Notice: Subject to any disclaimer, the term of this patent is extended or adjusted under 35 U.S.C. 154(b) by 734 days.

(21) Appl. No.: 13/209,316

(22) Filed: Aug. 12, 2011

(51) Int. Cl.
*A61B 5/097* (2006.01)
*A61B 5/08* (2006.01)
*A61B 5/087* (2006.01)

(52) U.S. Cl.
CPC .............. *A61B 5/097* (2013.01); *A61B 5/082* (2013.01); *A61B 5/087* (2013.01); *A61B 5/0878* (2013.01)

(58) Field of Classification Search
CPC ......... A61B 5/097; A61B 5/087; A61B 5/082; A61B 5/0878
USPC ................... 600/529, 537, 538, 543
See application file for complete search history.

(56) References Cited

U.S. PATENT DOCUMENTS

| 5,167,506 | A |   | 12/1992 | Kilis et al. |
| 5,277,196 | A | * | 1/1994  | Hankinson ............ A61B 5/087 600/537 |
| 5,518,002 | A | * | 5/1996  | Wolf .................... A61B 5/0878 482/13 |
| 5,578,753 | A | * | 11/1996 | Weiss et al. ............... 73/335.02 |
| 6,398,727 | B1 |  | 6/2002  | Bui et al. |
| 6,942,625 | B1 |  | 9/2005  | Bryant |
| D541,419  | S |   | 4/2007  | Jones, Jr. |
| 2002/0138017 | A1 | * | 9/2002 | Bui et al. ................. 600/537 |
| 2003/0216659 | A1 | * | 11/2003 | Brawner ............. A61B 5/0871 600/532 |
| 2005/0165322 | A1 |   | 7/2005 | Bryant |
| 2006/0100537 | A1 | * | 5/2006 | Williams et al. ............. 600/538 |
| 2007/0191687 | A1 | * | 8/2007 | Justus ........................ 600/300 |
| 2007/0234730 | A1 | * | 10/2007 | Markham et al. ............. 60/772 |
| 2008/0030317 | A1 |   | 2/2008 | Bryant |
| 2010/0204602 | A1 | * | 8/2010 | Addington et al. .......... 600/538 |
| 2010/0305466 | A1 | * | 12/2010 | Corn ........................... 600/538 |

OTHER PUBLICATIONS

Young et al., "Forced Expiratory Volume in One Second: Not Just a Lung Function Test But a Marker of Premature Death From all Causes," European Respiratory Journal, 30:4, pp. 616-622, Feb. 2007.

(Continued)

*Primary Examiner* — Puya Agahi
(74) *Attorney, Agent, or Firm* — Lempia Summerfield Katz LLC

(57) ABSTRACT

A health risk assessment device includes a mouthpiece, a flow path in fluid communication with the mouthpiece, a sensor disposed in the flow path and configured to generate a representation of a spirometric parameter of air flow in the flow path exhaled by a user through the mouthpiece, a user interface configured to allow the user to provide user profile data including smoking history data, and a processor coupled to the sensor and the user interface and configured to determine an output indicative of a risk that the user develops a respiratory, cardiopulmonary, or cardiovascular disease based on the spirometric parameter representation and the smoking history data.

33 Claims, 5 Drawing Sheets

(56) References Cited

OTHER PUBLICATIONS

Morris et al., "Short Report: Spirometric "Lung Age" Estimation for Motivating Smoking Cessation," Preventive Medicine, vol. 14, pp. 655-662, 1985.
Product literature, Micro Direct, Inc., "Digital Peak Flow Meter for Spirometry," www.micro-direct.com, one sheet (2010 or earlier—see first paragraph).
Parkes et al., "Effect on Smoking Quit Rate of Telling Patients Their Lung Age: The Step2quit Randomised Controlled Trial," British Medical Journal, pp. 1-7, Mar. 6, 2008.
Product specification, Vitalograph copd-6, www.vitalograph.com/products/copd-6_technical_data.php, one sheet, Jun. 21, 2011 (copyright 2007-2010).
Product literature, Vitalograph copd-6, www.vitalograph.com/products/cops-6.php, one sheet, Jun. 21, 2011 (copyright 2007-2010).
"User Manual," Vitalograph copd-6™ usb model 4000, issue 1, pp. 1-22, 2008.
Vitalograph copd-6™ usb model 4000 user manual, issue 3, pp. 1-16, 2007 & 2008.
Product brochure, "The Satellite/Base Station," Jones Medical Instrument Co., 2 sheets, 2001.

\* cited by examiner

SPIROMETRY-BASED PERSONAL HEALTH RISK ASSESSMENT DEVICE

BACKGROUND OF THE DISCLOSURE

Field of the Disclosure

The disclosure relates generally to medical devices and, more particularly, to spirometers.

Brief Description of Related Technology

Cigarette smoking is a leading risk factor for several causes of death, including heart disease, lung cancer, chronic obstructive pulmonary disease (COPD), and stroke. Of those, COPD, which is caused by smoking, is often undiagnosed. COPD is a very slow and progressive disease. Airflow obstruction, the hallmark of COPD, is often present prior to other common COPD symptoms such as chronic cough and sputum production. But airflow obstruction is very gradual, during which time many smokers attribute their shortness of breath to aging and adjust their lifestyles accordingly, which further exacerbates the problem. By the time COPD symptoms are recognized, many patients have lost 50% of their lung function and now have moderate to severe COPD. Early identification of COPD can lead to smoking cessation, better quality of life, and significantly lower health care costs.

Early identification of COPD can be accomplished with a spirometer, which is a medical device designed to measure airflow obstruction. Unfortunately, many primary care physicians (PCP's) do not utilize spirometry testing. Physicians are also often not reimbursed for spirometry tests unless the patient is symptomatic, i.e. complains of shortness of breath, chronic cough, etc. As a result, COPD is rarely detected early.

The concept of "lung age" has been useful in making abnormal spirometry tests easier to understand for patients and in motivating smokers to quit. Lung age is determined from the spirometric measurement of the forced expiratory volume during one second of the expiratory maneuver (FEV1), i.e., the maximal amount of air one can forcefully exhale in one second. Lung age is the age of an average healthy person who has an FEV1 equal to the individual tested. Normal or predicted spirometric values, including FEV1, have been determined from large scale population studies based on a subject's age, height, sex, and race.

An inverse relationship between FEV1 values (e.g., decreasing) and cardiopulmonary risks (e.g., increasing) in smokers has been identified. Health care providers have been urged to evaluate and consider those patients with abnormal spirometry results for treatment of cardiopulmonary diseases (heart attack, stroke, COPD, and lung cancer). Unfortunately, the response has been limited by the low utilization of spirometry testing among health care providers.

Attempts to determine an individual's personal health risk are often based on answers to a health risk assessment (HRA) questionnaire. Most HRA questionnaires are limited to seeking demographic information (age and gender), lifestyle information (exercise, smoking, and diet), and physiology (weight, height, race). The risk analysis of HRA questionnaires is limited by the subjective nature of the data collected.

SUMMARY OF THE DISCLOSURE

In accordance with one aspect of the disclosure, a health risk assessment device includes a mouthpiece, a flow path in fluid communication with the mouthpiece, a sensor disposed in the flow path and configured to generate a representation of a spirometric parameter of air flow in the flow path exhaled by a user through the mouthpiece, a user interface configured to allow the user to provide user profile data including smoking history data, and a processor coupled to the sensor and the user interface and configured to determine an output indicative of a risk that the user develops a respiratory disease based on the spirometric parameter representation and the smoking history data.

In accordance with another aspect of the disclosure, a health risk assessment device includes a mouthpiece, a flow path in fluid communication with the mouthpiece, a sensor disposed in the flow path and configured to generate a representation of a spirometric parameter of air flow in the flow path exhaled by a user through the mouthpiece, a user interface configured to allow the user to provide user profile data, and a processor coupled to the sensor and the user interface and configured to determine an output indicative of a risk that the user develops a cardiovascular disease based on the spirometric parameter representation and the user profile data.

In accordance with yet another aspect of the disclosure, a health risk assessment device includes a mouthpiece, a flow path in fluid communication with the mouthpiece, a sensor disposed in the flow path and configured to generate a representation of a spirometric parameter of air flow in the flow path exhaled by a user through the mouthpiece, a user interface configured to allow the user to provide an age of the user, and a processor coupled to the sensor and the user interface and configured to determine an output indicative of a lung age gap based on the spirometric parameter representation and the age of the user.

BRIEF DESCRIPTION OF THE DRAWING FIGURES

For a more complete understanding of the disclosure, reference should be made to the following detailed description and accompanying drawing figures, in which like reference numerals identify like elements in the figures.

Figure 6:
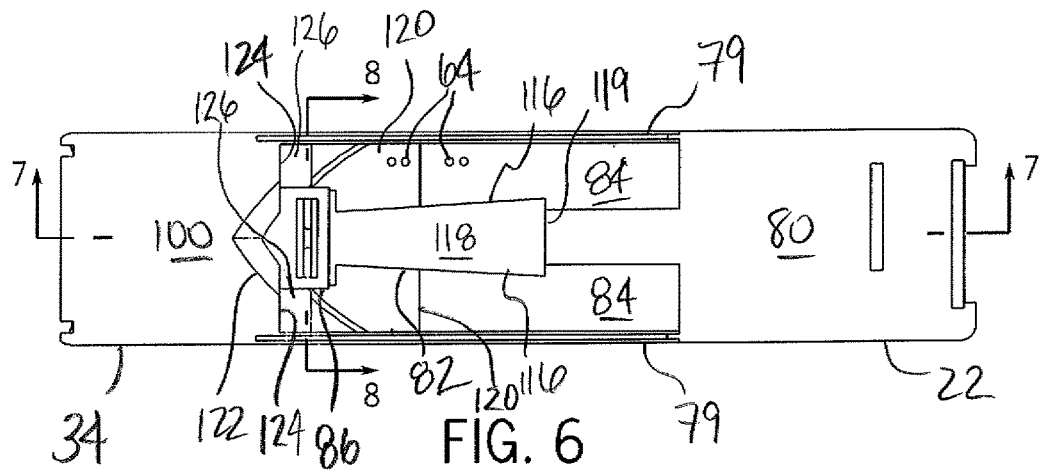
FIG. 6 is a plan view of the spirometer flow path component of FIGS. 4 and 5.
Figure 7:
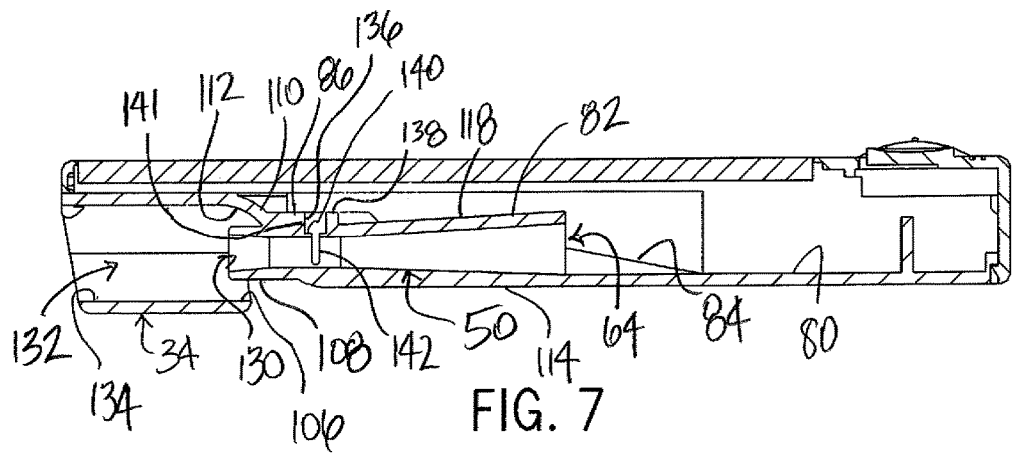
Figure 8:
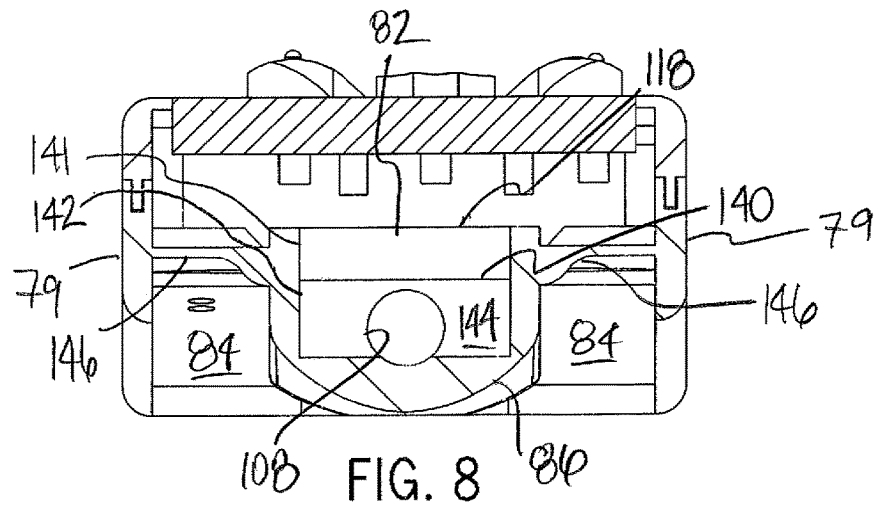

FIGS. 7 and 8 are sectional view of the spirometer flow path component taken along lines 7-7 and 8-8 of FIG. 6, respectively.

Figure 9:
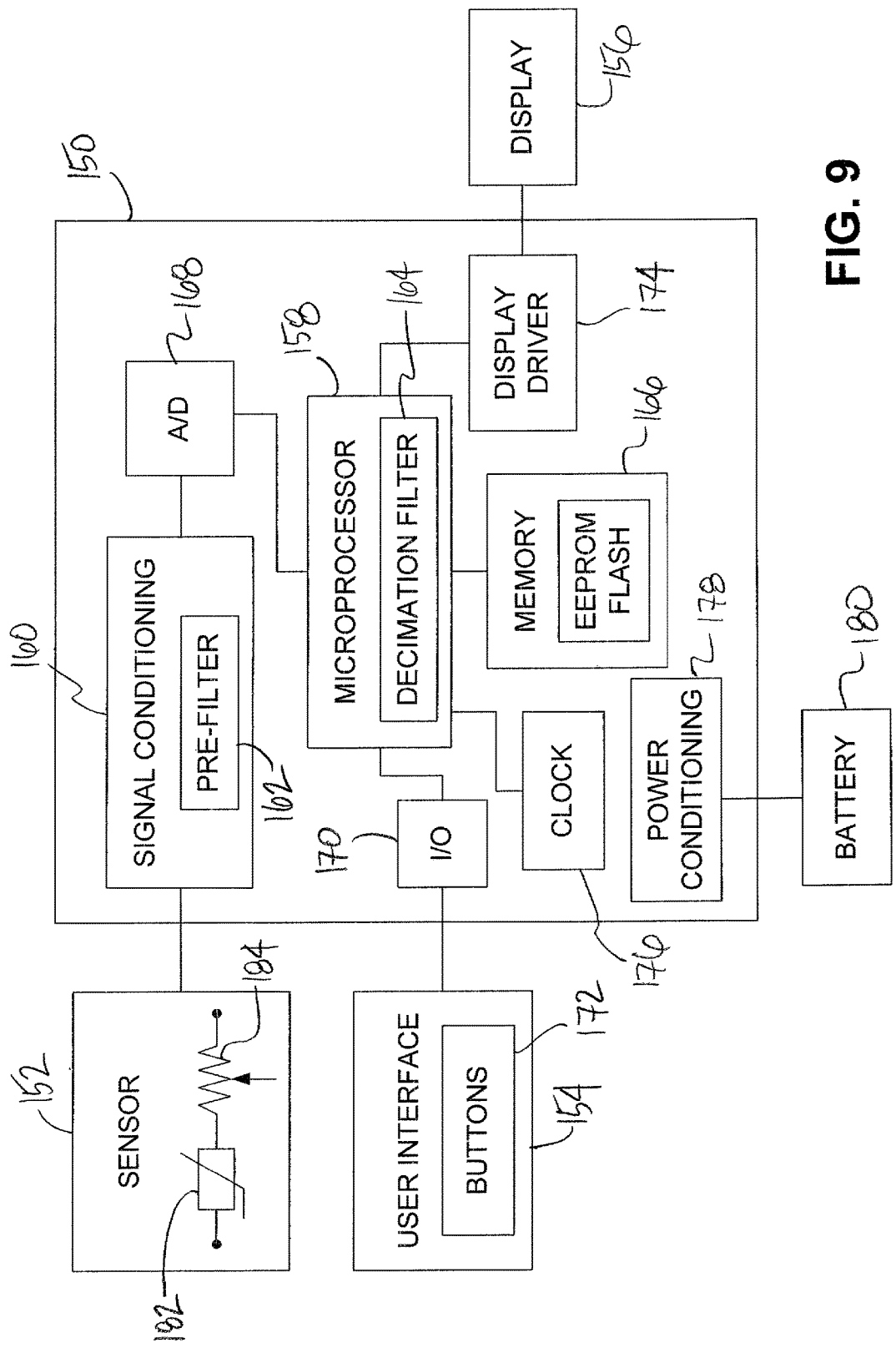

FIG. 9 is a block diagram of exemplary circuitry configured to control operation of the disclosed personal health risk assessment devices.

Figure 10:
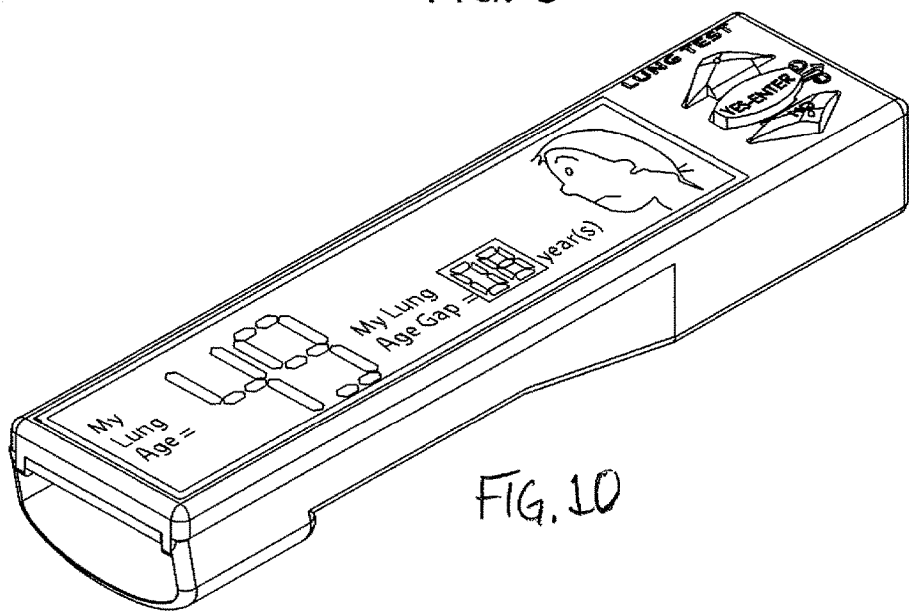

FIG. 10 is a perspective view of another example of a personal health risk assessment device constructed in accordance with an embodiment directed to provide a lung age gap assessment.

While the disclosed devices are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF THE DISCLOSURE

The disclosure generally relates to personal health risk assessments based on spirometric or pulmonary function measurements. Inexpensive and easy-to-use personal health risk assessment devices are described. The disclosed devices may be configured to capture a snapshot of lung function based on the forced expiratory volume of air exhaled in one second (FEV1).

The devices are configured to show patients that some aspect of their lung function may improve upon smoking cessation. The device may display a patient's personal risk for lung diseases as well as any other diseases associated with smoking. The majority of smokers want to quit and, in fact, make an attempt every year. With knowledge of their lung function (good or bad), smokers achieve higher twelve month quit rates. The disclosed devices provide users with knowledge of their personalized risks for respiratory, cardiopulmonary, cardiovascular, and other diseases, including acute forms or events of such diseases, such as heart disease, heart attack, COPD, stroke, and lung cancer. That knowledge may further increase quit rate success, insofar as these risks may be perceived as more serious consequences than decreased lung function.

The disclosed devices are configured as personal health risk assessment devices based on a spirometric parameter or measurement (e.g., FEV1). The devices may enable non-health care professional users to easily and inexpensively determine their own personal lung age, lung age gap, and/or one or more estimated health risks, such as the risk of COPD development, heart attack, and/or stroke. The marker (or biomarker) for each health risk assessment may be FEV1, a spirometric parameter defined as the maximum volume of air that can be exhaled in one second.

The disclosed devices may be configured in a manner suitable for personal, non-professional use. In order to achieve widespread personal use, the disclosed devices differ in a number of ways from common spirometers, which are designed for medical professionals. Spirometers provide complicated measurements and are often cost-prohibitive for consumers. The disclosed devices are configured for consumer friendly operation (e.g., three-button operational controls without written instructions but with test quality monitoring, feedback and prompts) by an average smoking consumer (e.g., age ≥40 years of age). The disclosed devices may be configured to display risk assessment information in an easily comprehended, yet impactful, manner (e.g., via a large display screen with animation), and base the risk assessments on spirometric data no less accurate than professional devices. The disclosed devices may be configured for handheld, battery or other low-power operation with automatic shutdown and other power-saving features.

The disclosed devices may be configured to take advantage of the personal aspect of the device. The devices may not be intended for use by multiple subjects. As a result, the disclosed devices may avoid the need for a sensor, a flow chamber, and/or a mouthpiece that are physically and/or hermetically separable from the rest of the device. These components of spirometers are typically disposable for hygienic reasons, yet still configured for effective operation. Avoiding the multiple-user context may also lead to benefits involving reduced requirements for validation, testing, customization, calibration, and other operational efforts. The single-user context may also simplify software design, memory management, and testing protocols.

The disclosed devices may include a thermistor-based sensor in contrast to the pressure transducer designs of typical spirometers. Replacement of the pressure transducer with a thermistor may also remove the need for a solenoid, further reducing the cost of the device. As described below, any inaccuracies that may be introduced by the thermistor-based sensor may be addressed via one-time, manufacturer calibration because of the uniformity of the exhalation air temperature and proximity of the thermistor to the subject's mouth.

The disclosed devices may be configured to estimate risk of developing respiratory, pulmonary, cardiopulmonary, and/or cardiovascular diseases, and, as a result, may differ from—diagnostic devices in a number of ways. For example, diagnostic devices may be limited to determining one or more parameters (e.g., a degree of impairment or obstructive index value) necessary to diagnose and/or classify the severity of the disease. Other information or data may be useful in measuring or determining the risk of developing a disease. The output and other user interface aspects of the disclosed devices may also differ from diagnostic devices in the type of, and manner in which, information is provided to the user. For example, the disclosed devices may avoid display or use of complex medical terms such as FEV1, FEV6, and FVC or "percent of predicted" in estimating risk. The devices are thus configured to provide risk information in terms that users find easy to understand, including, for example, percent of normal, probability of developing a certain disease within the next 10 years, probability of having a heart attack or a stroke within the next 10 years, lung age, and lung age gap.

Armed with the objective information of personal estimated health risk, a user may be encouraged to share this information with a health-care provider and to consider a behavioral or lifestyle change (i.e., diet, smoking cessation, and/or therapeutic intervention) as a preventative measure. Providing individualized risk of disease may be useful in that it offers the opportunity for preventative measures via modification of risk factors (e.g., smoking cessation). Onset of the disease may be prevented via such early or timely, easy-to-understand, objective feedback on lung function, and users thereby avoid waiting until a physician-driven diagnosis that comes too late.

Although described in connection with a number of exemplary embodiments directed to COPD, the disclosed devices may be useful in connection with other respiratory diseases (e.g., lung cancer and other pulmonary diseases), and cardiopulmonary or cardiovascular diseases. Small decrements in lung function (e.g., FEV1) are associated not only with pulmonary morbidity and mortality, but also with other causes of morbidity and mortality, e.g., those of the cardiovascular nature, such as stroke and heart attack. COPD, cardiovascular disease and even lung cancer may result from inflammatory responses in the lung and that the individual responses to these processes are genetically determined.

Some of the devices constructed in accordance with the disclosure, such as those directed to estimating risk of cardiovascular diseases (e.g., stroke, heart attack) and lung cancer, may use FEV1 or other spirometric data (e.g., percent of predicted FEV1) as the primary or sole risk factor. Other devices, such as those directed to estimating COPD risk, may be configured to use the FEV1 or other spirometric data in combination with other data not involved in determining the predicted FEV1 (e.g., subject age, gender, etc.). For example, the risk of developing COPD may be estimated based on the number of cigarettes smoked daily in addition to the FEV1 data. The risk of developing COPD may also be estimated based directly on age, in addition to indirectly as part of the predicted FEV1 data.

Figure 1:
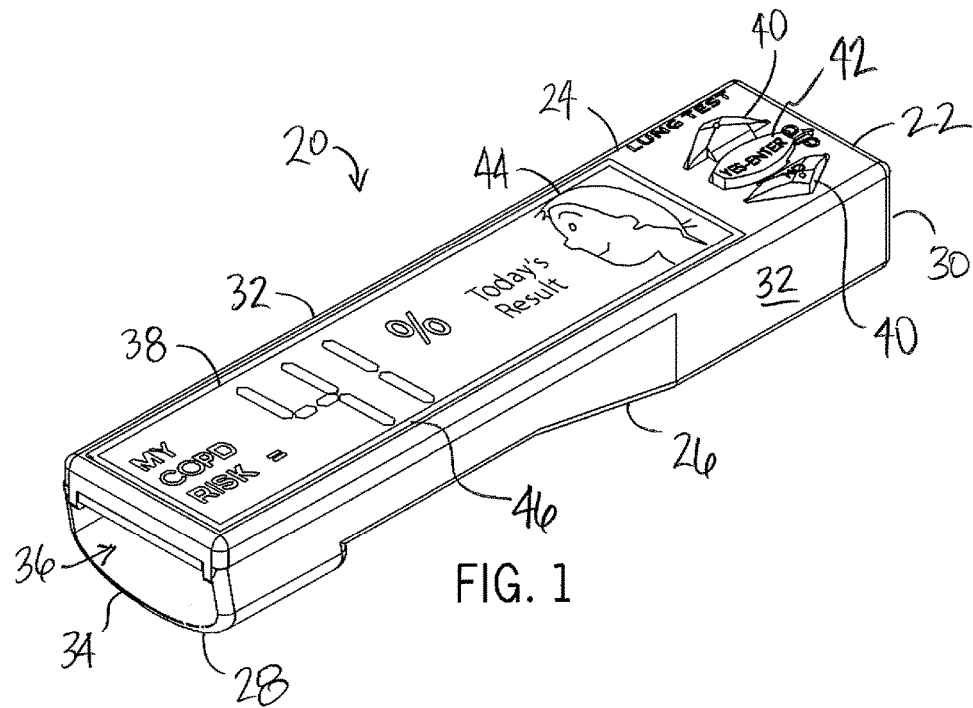
FIG. 1 is a perspective view of one example of a personal health risk assessment device constructed in accordance with one or more aspects of the disclosure.

With reference now to the drawings, FIG. 1 shows a portable health risk assessment device 20 constructed in accordance with one embodiment. The portable device 20 includes a housing 22 configured to be handheld. The housing 22 may have an elongate shape. In this example, the housing 22 is shaped such that the device 20 has a bar-shaped form factor, with a front or top side 24 opposite a rear or bottom side 26, an open end 28 opposite a closed end 30, and a pair of opposed lateral sidewalls 32. The open end 32 is configured as a mouthpiece 34 with an inlet 36 integrated with the remainder of the housing 22. The mouthpiece 34 in this example does not extend outward beyond the remainder of the housing 22. In other embodiments, the housing 22 need not be elongate or bar-shaped, and may include an extension or other projecting component configured as a mouthpiece.

The components of the device 20 may be constructed as an integral unit. For example, the mouthpiece 34 forms a part of the housing 22, and is thus not removable or detachable from the remainder of the unit. All of the components of the device 20 are contained within or disposed along the external surfaces or boundaries of the housing 22 in this example. The housing 22 and components contained therein may also form an integral unit with no moving parts. The device 20 thus has a solid, robust construction.

The device 20 is configured for handheld operation. The housing 22 may be held during installation or customization, as well as during a measurement or test. The sidewalls 32 provide faces near the ends 32, 34 for users to engage with their fingers. Tacky, rubberized, or other surfaces may be provided along the faces to improve grip.

The front side 24 includes a display screen 38 to provide output, instructions, and other information to a user. In this example, the display screen 38 is shaped as a panel disposed along the front side 24. The display screen 38 may include a liquid crystal display screen, the size of which may be maximized for a given size housing. Any type of display may be used. The display screen 38 forms a part of a user interface of the device 20 that may include any number of user interface elements to support input/output (I/O) functions. A number of directional buttons 40 are disposed on the front side 24 adjacent the display screen 38. A further button 42 may be provided to support a user-select or other function of the device 20. An operator may use the directional buttons 40 to navigate through a list or other set of items displayed on the display screen 38, and then use the user-select button 42 to choose a highlighted item. In this way, the user can initiate a test or implement some other function identified via the display screen 38. One or both of the directional buttons 40 may be configured with alternate functions (e.g., "no") to provide a user with further user interface options. The buttons 40, 42 may be formed from the same material as the housing 22, and may be constructed and configured for deflective or other touch-sensitive operation.

The display screen 38 may be configured to present a variety of operational instructions and other output information. The instructions may be useful in making the device 20 more user friendly. A section 44 of the display screen 38 may include an icon or other non-textual display element to provide information on how to properly use the device 20. The icon section 44 or other instructions provided by the display screen 38 may also be useful in helping to ensure that the user is blowing into the mouthpiece 34 properly and otherwise providing good data. For example, an animated display via the icon section 44 may improve compliance, procedure adherence, and, thus, test results. The display screen 38 may include another section 46 for providing operational feedback, including coaching, the results of a recent test (e.g., "Results look good"), test trend information, other messages such as "Call physician," "Schedule physician appointment" or "Seek immediate help" etc. In this example, the section 46 is configured to provide a risk assessment of developing COPD within a certain period of time, e.g., 10 years. The risk assessment may be generated relative to the average risk of developing COPD given one or more biographical or demographical parameters (e.g., age, gender, etc.). In this case, the risk assessment identifies how much more the user is likely to develop COPD (e.g., 41% more likely than average). To support the determination of the COPD risk assessment, the user interface of the device 20 may be configured for user entry of the biographical, demographical, or other user data. For example, the display screen 38 may be configured to present a user profile input interface for the user to input age, gender, and other information via the buttons 40, 42. The display screen 38 may be optimized, customized, or otherwise configured for a specific disease risk assessment or other output (e.g., stroke risk, heart attack risk, COPD risk, lung age gap, etc.). Such user interface customization may simplify device operation, help avoid user confusion or error, and reduce controller complexity.

Figure 2:
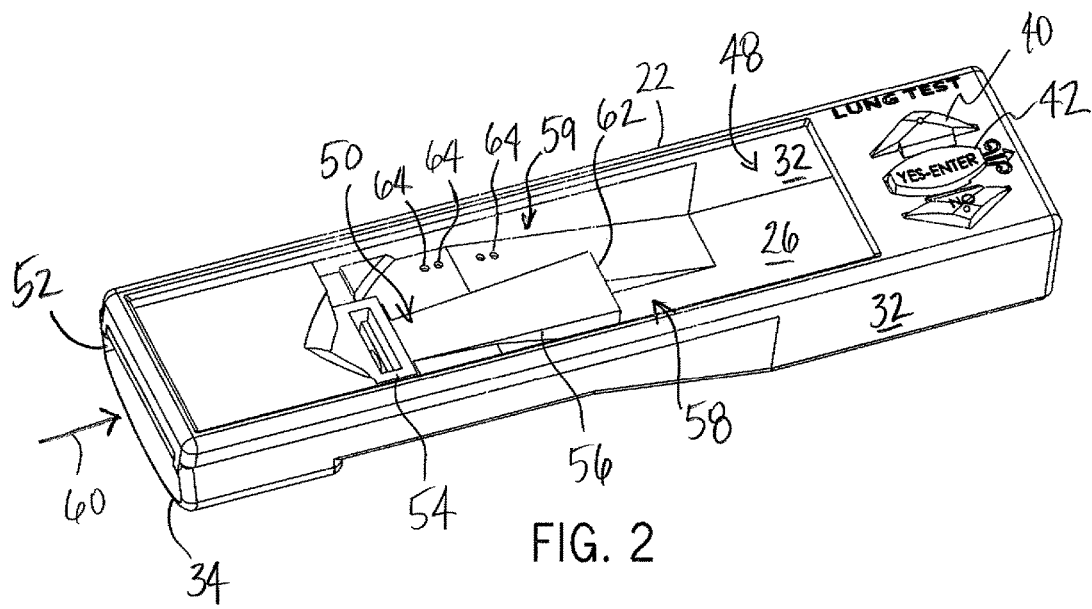
FIG. 2 is a perspective view of the personal health risk assessment device of FIG. 1 with a display screen removed to show a spirometer flow path component thereof in accordance with one embodiment.

FIG. 2 shows the device 20 without the display screen 38 to reveal an interior or internal chamber 48 within the housing 22. The internal chamber 48 generally corresponds with the inner space defined by the housing 22. The internal chamber 48 may have one or more openings or other regions not enclosed by the housing 22 when the device 22 is fully assembled. The internal chamber 48 is nonetheless defined by inner surfaces of the sidewalls 32, the rear side 26, and other surfaces of the housing 22, as well as the underside of the display screen 38. A number of components of the device 20 are disposed within the internal chamber 48, including, for instance, one or more printed circuit boards (PCBs), one or more batteries, etc. For example, a PCB (not shown) may be mounted within the chamber 48 adjacent a plastic or glass panel of the display screen 38 and/or the front side 24 of the housing 22 under the buttons 40, 42. While these and other components of the device 20 are housed within the internal chamber 48, the internal chamber 48 is also sized and configured to allow air exhaled during a measurement to flow within the housing 22. The exhaled air passes through the internal chamber 48 in part because the mouthpiece 34 is integrally formed with the housing 22 that defines the internal chamber 48.

Figure 4:
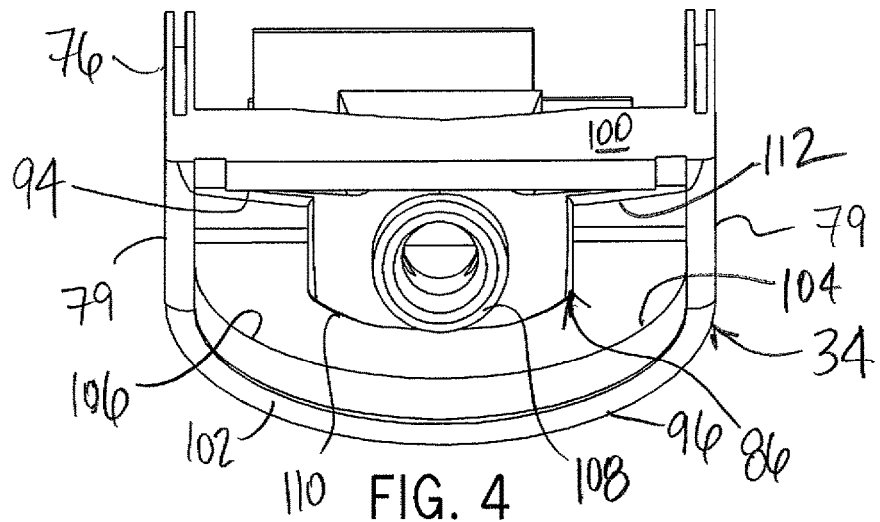
FIG. 4 is an end perspective view of the spirometer flow path component shown in FIG. 3 to depict an integrated mouthpiece and flow channel in accordance with one embodiment.
Figure 5:
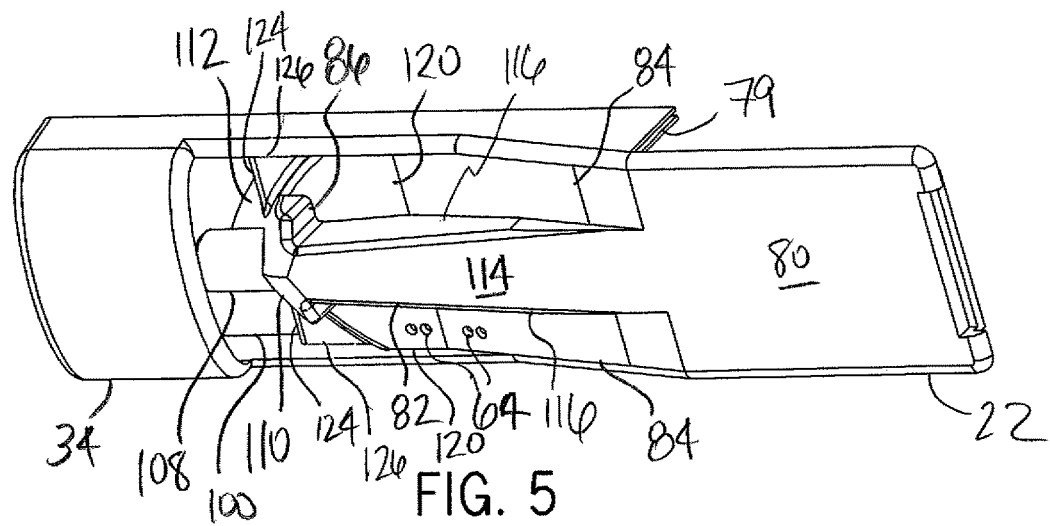
FIG. 5 is a bottom perspective view of the spirometer flow path component of FIG. 4 to depict the integrated mouthpiece and flow channel in further detail.

The internal chamber 48 includes and defines a spirometric flow path 50 of the device 20. The spirometric flow path 50 may correspond with a primary or main flow path of the device 20. Alternatively or additionally, the spirometric flow path 50 includes a secondary or auxiliary flow path of the device 20 also included within and defined by the internal chamber 48. In one example, the secondary or auxiliary flow path is a bypass flow path that routes exhaled air away from a primary or main flow path of the device 20. The secondary flow path may be disposed in parallel to the primary flow path and/or may be otherwise in communication with the primary flow path to sample the air flow exhaled by the user. More generally, the spirometric flow path 50 may include one or more open spaces in fluid communication with one another within the housing 22 through which the user's exhaled air passes during a measurement. Each segment or section of the flow path 50 may be internal relative to the housing 22, and thus protected from external disturbances or damage. For instance, the internal nature of the flow path 50 render the disclosed devices immune to distortion resulting from mechanical forces applied to the housing or outer casing that may be capable of distorting its shape (e.g., biting, squeezing, etc.). In this example, the flow path 50 includes an inlet segment 52 at the mouthpiece 34, a sensor segment 54, and a flow channel segment 56. The flow path 50 may also include an outlet segment 58 beginning at an end of the flow channel segment 56. The flow channel segment 56 may precede, follow, and/or include the sensor segment 54. The flow channel segment 56 may be configured to condition the flow to ensure measurements are taken within a large and stable region along the flow path 50. The sensor segment 54 may include or form a part of a flow chamber. In this example, the outlet segment 58 includes an exhaust region or space 59 downstream of the spirometric flow path 50. The exhaust space 59 is disposed within the housing 22 but external to the structural features that define the sensor and flow channel segments 54, 56. The spirometric flow path 50 may include one or more other segments, including, for instance, a sampling intake tube (FIGS. 4 and 5).

Air exhaled during a measurement enters the inlet segment 52 along a direction 60. Some of the exhaled air eventually passes through the sensor segment 54, at which time an indication of the velocity or one or more other characteristics of the exhaled air are captured. The air then passes through the flow channel segment 56 to reach the outlet segment 58. At this point downstream of the sensor segment 54, the air passes through an internal exhaust port 62 within the internal chamber 48. The internal exhaust port 62 serves as the transition between, and may be considered to be a part of one or both of, the flow channel segment 56 and the outlet segment 58. The internal exhaust port 62 may also be considered as the end of the spirometric flow path 50 of the device 20. As an internal port, the exhaust port 62 is not disposed at or along an external surface of the housing 22. In this example, the exhaust port 62 is disposed within the internal chamber 48.

In an alternative embodiment, a door is disposed along the flow path 50 to condition the air flow. The door may be configured as a restrictor plate despite the spirometric measurement involving a flow velocity determination. The flow may be restricted and conditioned because of the low velocities involved in the spirometric measurement. Low velocities may be sufficient due to a thermistor-based sensor, as described herein. The door may be disposed at the transition between the flow channel segment 56 and the outlet segment 58. In one example, the door is positioned at the exhaust port 62. More generally, the door may be configured as a separate, molded component discrete from the other components of the device 20. The door may be mounted or secured to one or more of the structures defining the flow path 50. In some cases, the door may be configured to almost entirely close off air from exiting through the exhaust port 62. The configuration of the door may be adjustable to tailor or customize the degree to which the air flow is blocked. The door may include a primary wall oriented transversely to the direction 60 of the air. The door may include one or more additional walls to provide, for example, support, further flow conditioning, etc.

The outlet segment 58 is configured to allow the exhaled air to exit the flow path 50. In this example, after exiting the internal exhaust port 62, the air flow reaches a dead-end within the internal chamber 48 of the housing 22. The dead-end occurs at an inner surface of the closed end 30 within the housing 22. The dead-end is reached if one were to continue in a straight line along the direction 60 after exiting the internal exhaust port 62. This aspect of the flow path 50 differs from the flow-through chambers typically found in spirometers, insofar as dead-ends are not typically found in spirometers. The air in the outlet segment 58 introduced by a measurement disperses within the housing 22 and may eventually pass back through the flow path 50 or bleed through various component gaps.

In this example, openings 64 are located alongside the flow channel segment 56. Each opening 64 may be used to provide access to electronics after the housing 22 has been assembled. For example, each opening 64 may be configured and positioned to allow a user to actuate a programming pin on an electronics component to reset or otherwise configure the component. The openings 64 may be formed in a recessed or elevated portion of the rear side 26 of the housing 22 behind the mouthpiece 34. Further details regarding the location of the openings 64 is set forth below in connection with FIGS. 5 and 6.

The absence of an external exhaust port along a non-recessed, external surface of the housing 22 may reduce or eliminate the possibility for debris contamination, obstruction, and other potential accuracy or operational problems. The device 20 may include one or more recessed exhaust ports, such as the exhaust port described below in connection with FIG. 4. In an alternative embodiment, one or more holes may be formed in the housing 22 to support an edge-tone and/or whistle feature, which may be directed to flow directionality detection and/or user feedback. The holes may be configured in a manner similar to the holes 64, or may be shaped as slots or other openings.

The flow path 50 may be configured for a velocity measurement. The sensor segment 54 and other aspects of the flow path 50 may be configured to detect the initial exhaust velocity of the air from the user as it passes through the flow path 50. In this example, the flow path 50 supports a direct velocity measurement rather than a flow rate measurement. As a result, the velocity of the exhaust air is not determined from, or based on, an assumed velocity profile. The direct velocity measurement may simplify the software and/or electronics of the device 20 because the velocity profiles for each test condition (or all test conditions) need not be stored or otherwise available for use or application. The direct velocity measurement may also be useful because the measurement is not subject to near-wall variations that would arise from slight variations in the flow channel. Such variations may occur as a result of normal production tolerance during, e.g., injection molding. The direct velocity measurements may then be used without corrections for such wall effects. Details regarding other useful characteristics of the flow path 50 (different flow resistances or other possible features for exhalation vs. inhalation detection, etc.) are set forth below. Notwithstanding these possible benefits, the flow path 50 may be configured in other embodiments to indirectly capture the velocity via a flow rate measurement. Alternatively or additionally, the flow path 50 may include multiple sensor segments.

The flow path 50 (e.g., the structures defining the flow path 50) is configured to assure a uniform velocity distribution across the sensor segment 54 so that slight variations in manufacturing and the placement of the sensor are inconsequential. The velocity distribution is uniform over the majority of the cross sectional area. Velocity may be measured directly without introducing error that would otherwise arise through placement in a variable velocity distribution. The uniformity of the flow path 50 may be based on result of flow acceleration and minimal boundary layer growth. As a result of the tapering or channeling down of the converging section 130, flow acceleration through the converging section 130 may flatten the velocity profile, reduce the boundary layer to maximize velocity uniformity at the sensor, and linearize the flow.

Figure 3:
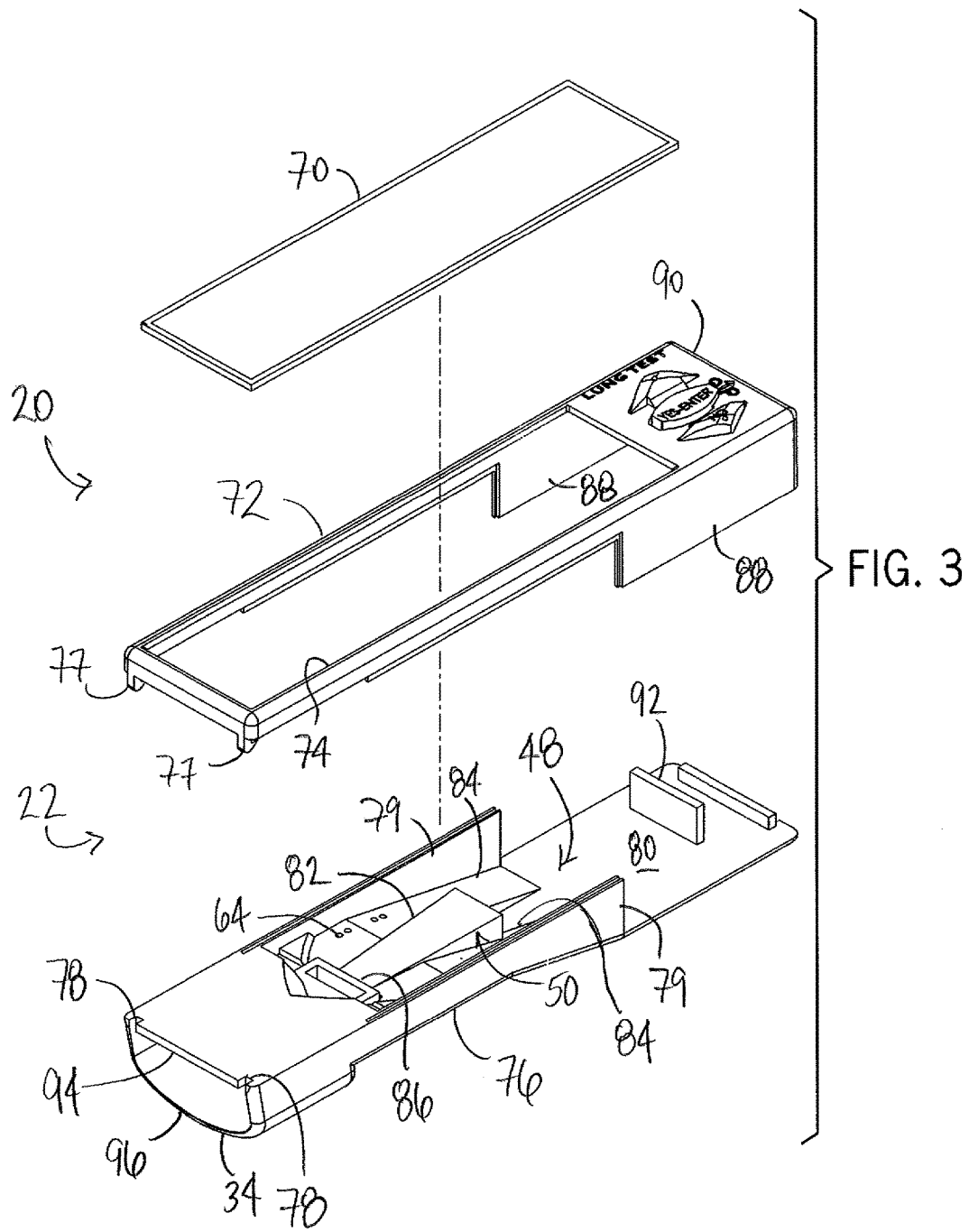
FIG. 3 is an exploded view of the personal health risk assessment device of FIG. 1 to show a one-piece construction of the spirometer flow path of the personal health risk assessment device of FIG. 1 in accordance with one embodiment.

FIG. 3 shows the device 20 in an exploded view to depict the assembly thereof. A display screen panel 70 may be secured to a cap 72 of the housing 22. The cap 72 includes an opening 74 in which the panel 70 is received. The panel 70 and the cap 72 may be fixed to one another via an adhesive or other fastener(s). Alternatively or additionally, the panel 70 may be fixed to the cap 72 via an interference fit with the opening 74, or may be larger than the opening 74 to be held in place within the opening 74 upon assembly of the device 20. Alternatively, the cap 72 is injection molded with the panel 70 from a clear plastic material as a single piece. The housing 22 also includes a base 76 configured to engage the cap 72. The base 76 in this example is configured with a number of structural features to be operable as a spirometric flow path component of the device 20. The flow path structures may be alternatively or additionally formed in the cap 72. The components of the housing 22 may be assembled via, for instance, a snap-fit or other interference fit connection between the cap 72 and the base 76. For example, the cap 72 may have a pair of snap hooks 77 on one end configured to engage matching detents 78 on the base 76. One or more other interfaces between the cap 72 and the 76 may be grooved or otherwise shaped for secured engagement. One or more fasteners may alternatively or additionally be used to secure the cap 72 and the base 76 to one another.

Both the cap 72 and the base 76 may be molded components made of plastic or other rigid material. For example, the cap 72 and the base 76 may be formed as discrete, unitary structures via injection molding. Each of the cap 72 and the base 76 may thus be of one-piece construction. The structural features of the device 20 that form a spirometric flow path may thus be of one-piece construction. Each component may be formed using other processes, and need not be made of the same material. A number of elements of these components are described below as distinct from one another with the understanding that the elements of the component may constitute structural features of a single, integrated, molded component rather than discrete parts. Notwithstanding the foregoing, one or more elements of the components may alternatively be separately formed to constitute a discrete part secured to the remainder of the component as a structural assembly.

The base 76 may be molded or otherwise shaped to define the internal chamber 48 and each segment of the flow path 50. For example, opposed sidewalls 79 of the base 76 define lateral outer boundaries of the internal chamber 48, while a panel 80 defines a lower outer boundary. Within these outer boundaries, the base 76 has a number of features that integrally define the segments or sections of the flow path 50. In this example, the flow path 50 includes a tapered duct 82 disposed between a pair of ramps 84 adjacent the duct 82, and a sensor mount 86 upstream of the tapered duct 82. The sensor mount 86 is disposed along the flow path to position a sensor, e.g., a thermistor, in a flow chamber well suited for spirometric measurements. The tapered duct 82 may be shaped to ensure that the inhalation flow resistance differs from the exhalation flow resistance. In this way, the device 20 avoids the need for a second sensor disposed in the flow path 50 to distinguish between inhalation and exhalation flows. The ramps 84 may be configured to provide a smooth surface or boundary for air flow across the bottom of the device for air exhaled by the user but not passing through the flow path 50. The ramps 84 may thus define part of a non-sensed flow path in parallel to the flow path 50. The non-sensed flow path may be the primary flow path of the exhaled air in the sense that only a fraction of the exhaled air is routed through the flow path 50. The ramps 84 may provide a sloped transition between sections or structures of the housing 22 along the bottom of the device. A smooth flow along the device bottom may help avoid turbulence, eddies, or other flow disturbances or disruptions that may otherwise lead to back pressure or other impediments to the air entering the flow path 50.

In this embodiment, the cap 72 may also define the outer boundaries of the internal chamber 48 via sidewalls 88. The sidewalls 88 may be shaped to complement the sidewalls 78 of the base 76 such that, upon assembly of the base 76 and the cap 72, the sidewalls 78, 88 meet and engage to form the lateral sides of the housing 22. The cap 72 also includes an end panel 90 that forms the closed end of the housing 22, which may help direct the exhaust flow. The internal chamber 48 may also be defined by one or more upright walls 92 that project upward from the panel 80 to also help direct the exhaust flow. The upright walls 92 may alternatively or additionally act as dividers to separate the internal chamber 48 from other, non-flow-related chambers inside the housing 22, which may be configured as a cabinet for other components, such as a battery.

In this embodiment, the base 76 also defines the mouthpiece 34. The mouthpiece 34 is, thus, integrally formed with the rest of the flow path 50 and the other features of the base 76. The mouthpiece 34 may have a flat overhang 94 and a rounded floor 96 spaced from one another by the sidewalls 79. In this way, the mouthpiece 34 may be shaped in a manner that promotes a good measurement.

FIG. 4 shows the mouthpiece 34 and the inlet to the flow path 50 in greater detail. The overhang 94 is configured as a shelf 100 extending between the sidewalls 79. The rounded floor 96 is spaced from the shelf 100 by the sidewalls 79 and extends from an outer edge 102 to an inner edge 104, at which point an opening 106 is formed in the base 76. The opening 106 allows a significant portion of the user's exhalation to bypass an inlet tube 108. Only a fraction of the exhalation flow enters the inlet tube 108 for measurement. The inlet tube 108 acts as an entryway to the flow path, and may be integrally formed by the other segments thereof. The inlet tube 108 in this example is an integral part of the base 76. The inlet tube 108 may be suspended from the shelf 100 by the sensor mount 86, which may be configured as a cross-brace that projects downward from the shelf 100. As also shown in FIG. 5, the sensor mount 86 may include a front end 110 that faces the mouthpiece 34. The front end 110 may have a sloped or hull-shaped surface 112 that flares outward toward the outer edge of the shelf 100 to help reduce turbulence in the mouthpiece 34.

As shown in FIGS. 5 and 6, the duct 82 that forms the flow channel segment 56 of the spirometric flow path 50 has a width that expands as the air flow travels away from the sensor segment 54. The duct 82 may have a rectangular cross-section, with a bottom 114 (FIG. 5), a pair of opposed upright sidewalls 116, and a top 118 (FIG. 6). The duct 82 extends about halfway along the length of the ramps 84 to an end 119 at which the internal exhaust port 62 is formed. In this example, the internal exhaust port 62 may be configured as a rectangular opening disposed along the panel 80. The bottom 114 of the duct 82 may be contiguous with the panel 80, with a continuous, smooth transition between the two structural features. For example, the bottom 114 of the duct 82 may be level or even with the panel 80, forming a single flat surface over which the air flows along both sides of the housing (i.e., inside and outside). Other portions of the bottom 26 (FIG. 1) of the housing 22 are sloped with the inclination of the ramps 84 on either side of the duct 82, as shown in FIG. 5. This slope may help smooth that portion of the air exhaled from the user but not entering the flow path 50 as it passes either side of, and along, the bottom 114 of the duct 82, to reach the panel 80.

The front end 110 (FIG. 5) of the sensor mount 86 may be formed via a complementarily shaped depression 122 (FIG. 6) formed in the shelf 100. The shelf 100 terminates at the depression 122 and a pair of upright walls 124, which define an interior wall of the mouthpiece 34 alongside the intake tube 108 (FIG. 5). The walls 124 may also serve as dividers between the mouthpiece 34 and the internal chamber 48. The walls 124 form a front side of a pair of blocks 126 that encase the sensor mount assembly, which may be basically rectangular. The upstream or leading-edge of the blocks 126 may be shaped and smoothed to allow the airflow being exhausted through the mouthpiece to exit the opening 106 more quickly, with less disturbance.

FIG. 7 shows the spirometric flow path 50 in greater detail. A front opening or inlet section 130 of the intake tube 108 is disposed in a rear portion of a cavity 132 formed by the mouthpiece 34. In this example, the intake tube 108 necks down, narrows, or tapers radially inward, in the direction of the air flow toward a throat section of the flow path 50. The taper may be provided via an increased thickness in the walls of the intake tube 108. The cavity 132 includes a front opening 134 to receive the exhaled air during a measurement. The exhaled air is either captured by the inlet tube 108 via the front opening 130 or passes below the intake tube 108 to be exhausted via the opening 106 in the rear portion of the cavity 132. The exhaled air is directed toward one of the openings 106, 130 by the sloped surface 112 of the front end 110 of the sensor mount 86.

The size of the duct 82 in this example changes so that the flow channel segment 56 expands in the direction of the air flow. The duct 82 may taper outward both in width (as described above) and in height, as shown in FIG. 7. The flat top 118 of the duct 82 in this example is oriented on an incline as the air flow moves toward the internal exhaust port 64. The height of the duct 82 may also increase because an internal surface of the bottom 114 of the duct 82 slopes downward as the thickness of the bottom 114 decreases. One of the ramps 84 is shown as it slopes upward from the panel 80 adjacent the duct 82.

With continued reference to FIG. 7, the sensor mount 86 includes a slot 136 formed in an upper surface 138 of the mount 86. The upper surface 138 may be adjacent one or more circuit elements disposed near the user interface elements of the device, such as the LCD screen. In this way, wiring or other electrical connection can be made with a sensor (FIG. 10), such as a thermistor, disposed in the slot 136. In this example, the slot 136 includes a shelf 140 that defines two portions of the slot 136, a shallow, wide portion 141 above the flow path and a deep, narrow portion 142 that intersects the flow path. Electrical and structural connections, such as solder mounts, to each electrode of the sensor may be made in the shallow, wide portion above the shelf 140, which may act as a platform to support the solder mounts or other connections. A body of the sensor may be then suspended within the deep, narrow portion 142 of the slot 136 to position the sensor in the flow path for the velocity measurement. The sensor may thus be disposed directly in the flow path rather than along the flow chamber wall.

In an alternative embodiment, the housing 22 includes a grill or louver structure or other slatted component that runs along the bottom 114 of the duct 82 from the opening 106 to the panel 80. The grill may be configured to prevent a user from blocking the opening 106 with a finger(s), and/or help prevent other obstructions (e.g., debris-based obstruction). The grill or other component along the bottom of the housing 22 may include one or more molded indentations that define grip surfaces for a user. The indentations may be configured to conform to a user's finger as the device 20 is held. The indentations may help to indicate the correct position for the user's fingers during operation.

The cross-section of FIG. 8 shows the sensor mount 86 in greater detail, including the location of the shelf 140 below the top 118 of the duct 82 and above the intake tube 108. One of a pair of walls 144 that define the narrow portion 142 of the slot 136 is adjacent the intake tube 108. The sensor body may be centered or otherwise suspended in the intake tube 108 between the walls 144. The sensor mount 86 is, in turn, suspended from the sidewalls 79 via laterally extending structures 146 that form the floors 126 (FIGS. 5 and 6). The sensor body need not be centered. For example, the sensor body may instead may be attached to one of the sidewalls 79.

FIG. 9 shows one example of a control circuit or controller 150 configured to control the disclosed devices. The controller 150 is coupled to a sensor 152 to receive a signal representative of air flow to which the sensor 152 is exposed. The sensor 152 is disposed within or along the spirometric flow path at a position such that the signal is representative of initial exhaust velocity. The signal may then be used by the controller 150 to determine an output indicative of a risk that the user develops one or more diseases. To that end, the controller 150 may be configured to generate a representation of a spirometric parameter, such as FEV1, corresponding with the initial exhaust velocity of the air flow. The controller 150 is also coupled to one or more user interfaces 154 to obtain biographical, demographical, behavioral, or other data regarding the user. The controller 150 may also be configured to compare the measured spirometric parameter and an expected value of the parameter based on the user data. For example, the comparison may be indicative of a percentage of expected value (e.g., an FEV1 value=79% of normal for a given age, gender, smoking history, etc.). From that indication, the controller 150 may be configured to determine one or more risk assessments or levels. The controller 150 is coupled to one or more displays 156 or other user interfaces, such as the above-described LCD, to convey the risk assessment information to the user. The display 156 may be customizable or otherwise adjustable to accommodate different users. For example, the text size of the display 156 may be adjusted or configured to allow users with poor vision to read the output data. Alternatively or additionally, the disclosed devices may be configured with varying text sizes and other user interface characteristics based on the typical or expected age of the user (e.g., COPD subjects may typically be older, thereby calling for a larger display text size).

The controller 150 may include a processor 158, such as a microprocessor, configured to direct the above-described input/output (I/O) procedures and to implement the above-described measurement data processing to arrive at the risk assessments. The processor 158 may be configured to implement fixed point or floating point math. A fixed point configuration may be less memory-intensive, and may be more well suited for smaller microprocessors. The microprocessors commercially available from STMicroelectronics under model/part number STM32F103R8T6 may be used as the processor 158.

The controller 150 may include one or more low-pass filters to process the flow velocity data collected by the sensor 152. Low-pass filtering may remove noise and other components of the velocity data signal not of significance to the spirometric determination. In some cases, the information needed from the sensor measurement lies in a frequency range between 0-15 Hz. Removal of frequencies above 15 Hz without affecting the determination of when peak flow occurs may be useful as such higher frequencies may undesirably impact the spirometric measurements. As described below, the filtering may be implemented in a number of stages, with one or more stages in the analog domain and one or more stages in the digital domain.

The flow velocity data collected by the sensor 152 may be first processed by a signal conditioning circuit 160, which may include a pre-filter 162, such as a third-order Butterworth filter. The pre-filter 162 may be a hardware analog filter configured to prepare the analog sensor data for digitization while introducing minimal phase distortion. The analog pre-filter 162 may be a lower order filter, such as a third-order filter. The analog filter 162 may have a low order that minimizes phase distortion, yet still removes unwanted frequencies. The analog filter 162 may be formed from discrete components, such as capacitors, resistors, and operational amplifiers.

The analog pre-filter 162 may be used in combination with further filtering in the digital domain by, for instance, a digital filter 164. The digital filter 164 may be configured as a low-pass digital filter with zero-phase delay. In some cases, the digital filter 164 is configured as a decimation filter. The processor 158 may be configured to implement one or more digital signal processing (DSP) procedures of the digital or decimation filter 164 stored in one or more memories or storage devices 166, such as a flash memory (e.g., EEPROM), random access memory (RAM), etc. The memory 166 may include volatile and/or non-volatile memory. The decimation filter 164 may be configured as a low-pass, direct form, finite-form finite impulse response (FIR), least-squares filter. In one example, the decimation filter 164 is configured as a zero phase delay 460 order filter. Together, the analog pre-filter 162 and the digital filter 164 process the analog flow velocity data in a manner that avoids aliasing effects and phase delay in the sampled output. The signal conditioning circuit 160 may alternatively or additionally include other filter topologies, including, for instance, higher order filtering in the analog domain. Alternative filter topologies include Bessel and Chebyshev filters.

The controller 150 may include one or more analog-to-digital converters 168 to sample the analog sensor data and couple the signal conditioning circuit 160 to the processor 158. In the example shown, the analog filter 162 and the digital filter 164 are coupled in series via the analog-to-digital converter 168 to process the incoming flow velocity signal. Alternatively, the analog-to-digital conversion is implemented by the processor 158 (e.g., as a part of a digital sampling and filtering procedure). More generally, such serial processing in both the analog domain and the digital domain differs from, and may have several distinct benefits over, the filtering techniques conventionally used in spirometers. The combination may significantly reduce the overall component cost (e.g., about 5%) because, for instance, a reduction in the order of the analog filter 162 leads to a reduction in the component costs of the analog filter 162, as well as an increase in tolerance for the precision of such components. The combination may significantly increase the space available on the printed circuit board upon which the components of the controller 150 are mounted because less components are used. The combination may include digital signal processing steps implemented by the processor 158, such as decimation. The combination avoids the data sampling distortion because the overall system phase distortion is minimized and anti-aliasing effects are minimized. The combination may achieve better accuracy than analog-only designs because the use of a digital filter allows for more stringent filter specification implementations than are possible with hardware-only designs.

The processor 158 may be configured to measure a dynamic time response of the sensor 152 over an extended period of time. The processor 158 need not assume that the flow will be steady state, in which, for example, changes in the flow are slower than the response of the sensor 152. In steady-state spirometric measurements, a second sensor may be used to measure ambient temperature to support a temperature compensation procedure implemented by the processor. Here, the sensor 152 instead measures a dynamically changing flow, in which the flow is not steady state or constant but changing rapidly—on the order of 14 liters/second. The sensor 152 may be sized and otherwise configured to present a sufficiently small thermal mass for a sufficiently fast response. The dynamic time response is measured by the processor 158 over a period of time that corresponds with the user's exhalation. The measurement may be continuous, rather than a one-shot measurement. The processor 158 may be configured to mathematically integrate the flow data to determine a volume. The volume data may then be used by the processor 158 to determine peak flow and other spirometric data.

The digital signal processing provided by the processor 158 may be used to implement noise rejection techniques. The minimal phase shift aspect of the filter combination may help to avoid distorting the peak flow determination. The digital filter 164 may be configured to sample at a frequency above the Nyquist frequency (e.g., 100 Hz). Such sampling may be implemented with only minimal phase shift in the data. With the use of a zero phase digital filter and low order analog filter, the determination of peak velocity can be determined accurately to within 10 milliseconds. A standard set by the American Thoracic Society (ATS) specification for sampling is every 10 milliseconds (i.e., a sampling rate of 100 Hz). The combination of analog and digital filtering described herein may allow the phase shift to remain lower than the sampling period so that the processor does not distort the time at which peak flow occurs.

The controller 150 may include one or more I/O interfaces to support communication with the sensor 152, the user interface(s) 154, and the display(s) 156. In this example, the controller 150 has an I/O interface 170 configured to recognize user actuation of one or more buttons 172 of the user interface(s) 154. The controller 150 also has an LCD driver circuit 174 to direct the display(s) 156. Other I/O interfaces may be directed to supporting universal serial bus (USB), Bluetooth, and other communications with a variety of peripheral and other devices. The controller 150 may also include other electronic circuitry to support the above-described operations, including a clock generator 176 coupled to the processor 158 and a power conditioning circuit 178 coupled to one or more batteries 180. The controller 150 may be configured to provide power to the above-described components, including the sensor 152, derived from the battery 180. The battery 180 may be rechargeable or non-rechargeable.

The I/O interfaces 170 may include a variety of different connectors or ports to support data communication with other devices, such as personal computers. For example, a Universal Serial Bus (USB) connector port may be disposed along the device housing to enable data to be downloaded during a physician visit. Alternatively or additionally, the I/O interfaces 170 may include one or more antennas to establish a wireless communication link via a desired protocol (e.g., Bluetooth) to support such data downloads and other transfers. These communications generally support interoperability of the disclosed devices with a wide variety of other electronic devices and systems. Via these I/O interfaces, data may be stored for a variety of reasons, including backup, trend and other analysis, etc. The data may include both the raw FEV1 data as well as the risk assessment output based thereon. The data type or format selected for transfer may be adjusted or tailored to the destination of the data communication (e.g., insurance company, physician, therapist, trainer, pharmacist, pharmaceutical company, wellness center, etc.). In this way, the user may see the data in user-friendly terms (e.g., Lung Age gap), but the transferred data supports more conventional analysis of the raw FEV1 data.

In alternative embodiments, the processing steps provided by one or more of the above-described components may be integrated with the other processes implemented by the processor 158. For example, the processor 158 may be configured as a system-on-a-chip or application-specific integrated circuit (ASIC) that provides analog-to-digital conversion, analog filtering, I/O interfaces, one or more memories, an internal clock, and/or power conditioning. Alternatively or additionally, one or more digital signal processing tasks handled by the processor 158 may instead be addressed by a discrete digital signal processor (DSP) in communication with the processor 158.

The sensor 152 may include a thermistor 182. The use of a thermistor-based sensor differs from conventional spirometers, which may use pressure sensors to obtain a flow profile from which velocity can be derived. Thermistor-based sensing also avoids the power consumption issues (e.g., greater than 20 Watts) presented by hotwire mass airflow sensors. Such high power consumption levels may be unsuitable for use with the battery-powered devices described herein. In some cases, the disclosed devices are configured for operation at only 0.135 Watts. The disclosed devices rely on thermistor-based sensing despite the limitations typically presented by thermistors when measuring dynamic air flows. Thermistors are typically used in relatively static or constant flow applications because of the slow response time of thermistors. In the past, thermistors were considered too slow to measure the rapid changes in flows presented by spirometry. Moreover, the response time of some thermistors could be decreased, but only through the application of very large amounts of power. In contrast, the thermistor 182 is configured for low-power operation, e.g., battery-powered operation. The thermistor 182 is also well-suited for the flow measurements described above because the flow path creates a laminar flow that removes vortexes (which may create inaccurate readings) and turbulence (turbulence may appear as high frequency noise). The thermistor 182 may be sized and otherwise configured for consistency with the characteristic time response of the air flow through the flow channel. Thermistor size is small relative to the flow channel characteristic length so that velocity spatial variations are insignificant. The mounting of the thermistor 182 across the flow channel also introduces essentially no artifacts in the flow conditions that would otherwise influence the sensor response (such as near wall or support effects).

In some embodiments, the sensor 152 only includes a single thermistor. The sensor 152 may have a single-thermistor architecture or construction. Relying on only a single thermistor is possible in connection with the disclosed devices because the disclosed devices are configured to remove the need for a temperature-sensing thermistor conventionally disposed outside of the flow path (e.g., to determine the temperature of the flow source). The sensor 152 is positioned within the flow path in proximity to the mouthpiece and, thus, the mouth of the user. The sensor 152 is sufficiently close to the user's mouth to minimize any environmental impact on the temperature of the air flow at the sensor 152. Moreover, the relative temperature of exhaled breath is sufficiently constant. Person-to-person variance in mouth temperature is minimal. The sensor 152 and, in particular, the thermistor 182 may also be calibrated for operation at that mouth temperature. For example, the thermistor 182 may be coupled to a calibration device of the sensor 152, such as a programming resistor 184. The programming resistor 184 may be directed to a one-time calibration of the thermistor 182 during manufacture of the disclosed devices. Such calibration may also help address any accuracy issues presented by the thermistor 182. In some cases, the operation of thermistors may vary by as much as ±25%. Such inaccuracy is not exhibited measurement-by-measurement, but rather between different off-the-shelf units. As a result, the one-time calibration via the programming resistor 184 may be sufficient to correct any inaccuracies. Together, the thermistor 182 and the programming resistor 184 may form a three-terminal device that allows the printed circuit boards (PCBs) and sensors to be interchangeable during device manufacture.

In some embodiments, the calibration of the sensor 152 may include a n-piecewise linear correction or calibration. For example, one or more calibration points may be directed to addressing different flow rates.

The calibration of the sensor 152 may also be simplified due to the integral nature of the disclosed devices (e.g., no separable or replaceable parts), which stems from the personal nature of the disclosed devices (e.g., no need to replace parts between different users). Calibration of the disclosed devices may occur on a device-wide basis. There is no need to separately calibrate subsystems or components of the device because no components can be removed. Calibration on a device-wide basis can instead address the aggregate effects of component variances, including, for instance, the thermistor, the flow chamber, the analog circuitry, etc. For these reasons, the component tolerances (e.g., flow path dimensions) also may be relaxed relative to conventional spirometers. Conventional spirometers also often require calibration on a user-specific basis. Not only is such individual user calibration not necessary, the single-user nature of the disclosed devices may also lead to efficiencies in the procedures implemented by the processor 158. For instance, the device is only configured to test and store data for one individual. Data management, user interface elements, user data entry, and limited processing predictions are some examples of the efficiencies resulting from the single-user context.

Relying on a single thermistor is also possible in connection with the disclosed devices because the flow path of the disclosed devices may be configured so that a separate thermistor need not be relied upon to determine the directionality of the flow. In past thermistor applications, yet another thermistor has been disposed in the flow media to detect the flow direction. The flow direction may be useful to avoid measurements of an inhalation rather than exhalation. In the examples described above, the flow path (e.g., the flow channel) has differing inhalation and exhalation flow resistances. The flow channel may be configured as a flow diode. For example, the resistance difference may be based in part on the configuration of one or more of the following structural features: the mouthpiece 34; the intake tube 108; the flow channel segment 56 (e.g., the duct 82); and, the internal exhaust port 62. Some of the features may be tapered or otherwise shaped to present a different flow resistance based on the flow direction. With these flow resistance differences, the controller 150 may be configured to differentiate between exhalation and inhalation.

Other embodiments may alternatively or additionally include other components or features to provide further differentiation or auxiliary signals representative of the flow direction. For example, an air shield may be provided along the flow path (e.g., on one side of the thermistor) to shield the thermistor from heat loss arising from air moving in one of the two directions. Another example may include a structural feature that acts as a tone generator or oscillator when air flows in one of the two directions. The frequency changes with the flow rate. The controller 150 may then be configured with an edge-tone detector or module to detect the oscillation created by the air flow. The edge-tone generator may be configured to make an audible tone at a pre-determined flow rate, i.e. make a noise at 3L/sec flow. The audible signal may then be further utilized as a quality control indication to the user, or made detectable, but inaudible.

In an alternative embodiment, an audible tone may be created by a slot or other structural feature of the device configured in a manner similar to a whistle. This approach differs from edge-tone generation in that the audible tone may occur at any flow rate for a given direction i.e. inhalation vs. exhalation, and may also be used as a quality control indication to the user. For example, the device may be configured to inform the user: "You should not hear a whistle during the test." Hearing a whistle may then be an indication to the user that he is inhaling from the device, and performing the test incorrectly. This whistle feature may be configured such that the whistle is detectable, but inaudible. In this example, here the amplitude changes with the subject's flow rate, but the frequency generally stays the same.

For both the edge-tone and the whistle methodologies, the device may include a microphone to detect the pre-determined frequency(-ies). The microphone may be configured, for example, to detect frequencies in a range outside of, or filtered from, the range of human voice frequencies. The microphone may, but need not, be placed in the flow path, and may for example be mounted on the printed circuit board over a hole in the exterior housing or case (e.g., similar to the holes 64). Still other embodiments may include a one-way valve or trap door feature along the flow path, or a thermocouple to detect differences in source air temperature to differentiate between exhalation (mouth temperature air) and inhalation (ambient temperature air). The use of a thermocouple may also serve to improve accuracy by compensating for differences in mouth temperature, if desired.

Notwithstanding the advantages of a single-thermistor configuration, the disclosed devices may utilize one or more additional thermistors in alternative embodiments. The additional thermistors may be disposed along or within the flow path, and/or disposed outside of the flow path. Such additional thermistors may be used, for instance, to improve accuracy. In one example, the disclosed devices may include a two-thermistor arrangement with a heat well, the components of which may be fabricated via bulk or surface micromachining techniques. The thermistors and heat well may be provided as part of a micro-electromechanical system (MEMS) flow chamber. Such MEMS-based thermistor structures may be operable as a thermal convection or dissipation module or a thermal mass flow meter. To these ends, the MEMS components may be mounted directly onto the printed circuit board in place of the thermistor or alternatively on a Kapton or other structure for positioning within a flow path or chamber. Such MEMS sensors may be examples of embodiments having a sensor(s) mounted in a non-centered position within the flow path. Additionally or alternatively, the MEMS component may be configured to detect specific gas composition levels (CO, NO, etc.), which may provide indications of symptoms relating to personal risks (e.g., smoking behavior, asthmatic hyper-reactivity, etc., respectively).

The thermistor 182 and, more generally, the sensor 152, may be configured as non-temperature regulated devices. Avoiding the need for temperature regulation may simplify the construction of the device and minimize power consumption. The sensor 152 need not rely on measuring the heat from an external heat source proximal to the thermistor 182 blown into its detection range. The sensor 152 may instead be configured to measure the heat dissipation from itself. The sensor 152 may be configured as a constant temperature anemometer. The power delivered to the sensor 152 varies with the air velocity experienced by the sensor 152. A measurement of the velocity is determined based on the power provided to the sensor 152 to maintain it at a constant temperature.

The thermistor-based sensor 52 may provide a number of other advantages over pressure measurement-based spirometers. The thermistor-based sensors may be configured to be insensitive to barometric variations or gas density due to altitude, etc., or other ambient variations like humidity within the range of interest. For example, the operational temperature of the thermistor may be set to a level (e.g., 160 C) at which the sensor becomes relatively insensitive to barometric variations. Alternatively or additionally, the calibration of the thermistor at mouth temperature may also decrease the barometric sensitivity of the sensor. As a result of the barometric insensitivity, the disclosed devices may be factory calibrated without regard to the use location (e.g., without the need for recalibration). Thermistor-based sensors may also measure velocity directly in the flow path, rather than on the flow chamber wall. The sensors can measure velocity without the compensation involved in pressure-based measurements. The thermistor-based sensor is also less susceptible to errors resulting from dimensional variations in the flow chamber or from imprecise positioning along the flow path. The flow channel may be designed to have a uniform velocity distribution, across the flow, at the location of the sensor, so variations in sensor positioning and manufacturing tolerances do not affect the response. The tooling and processing during production may be significantly simplified. Moreover, thermistor-based sensors have reduced mechanical complexity, with no moving parts. Indeed, the disclosed devices may be essentially solid-state designs, which reduce the possibility for contamination, sensor inertia, vibration-based errors, etc. The disclosed devices are mechanically robust for these and other reasons, as described above in connection with the internal nature of the flow path.

In some embodiments, the thermistor 82 may be the thermistor commercially available as one of the products in the 111 series from Honeywell International, Inc. The thermistor 82 may be hermetically sealed in glass. The thermistor 82 may have a response time of approximately 0.5 seconds. Other commercially available thermistors, such as non-coated or ruggedized thermistors, having similar response times may be used. The thermistor 82 may have a resistor bead or body size on the order of $1/10^{th}$ of a millimeter (e.g., about $3/10^{th}$ of a millimeter) and a wire size on the order of $1/100^{th}$ of a millimeter (e.g., about $3/100^{th}$ of a millimeter). Such small dimensions may help increase the responsiveness of the thermistor 82 to detect the dynamic flows characterized by the spirometric parameters relied upon by the disclosed devices. The thermistor 82 may thus be a so-called "small-bead," "miniature-bead," or other "small-size" thermistor as distinguished in the art from "standard bead" thermistors. The thermistor current may be set to a maximum level for a given off-the-shelf thermistor to reach a high operating temperature, which may help to reduce ambient temperature and other environmental errors.

Handling and mounting such small thermistors presents challenges. The small sensor bead or body is very difficult to see with the naked eye, and generally should not be handled directly because of the hermetically sealed, thin glass coating. The wire size is even smaller and far more difficult to see with the naked eye. The wires also have a curly or random spring-like quality to them, resulting in a non-uniform part-to-part shape which is extremely difficult for both humans and even leading-edge machine vision and production capabilities. This makes the thermistors very difficult to handle, store and process at all stages of production. The extremely thin wire also can be fatigued easily if mishandled, causing the wires to break. The above-described controller (e.g., hardware and/or software) may be configured to detect damaged sensors in-circuit, as it would be virtually impossible to detect otherwise.

Further challenges may be presented because conventional thermistor mounting techniques may be unsuitable for the disclosed devices. For example, mounting on a side wall may be problematic because (1) the side wall acts as thermal sink to the thermistor, (2) the air flow on the side wall is influenced by manufacturing tolerances of the flow chamber, and (3) the amount of flow available for measurement is less than in the center area of the flow chamber. There are only two typical mounting options available from the manufacturers, and both of those are far too large to fit within our product. Mounting the thermistor onto conventional or industry standard fixtures, mountings and/or assembly trays has been found to be unworkable.

One exemplary thermistor mounting method includes soldering the sensor bead between two parallel metal pins, held in place by a plastic carrier, forming an 'H' shape. The sensor wires are then soldered to the pin-ends at the top of the H, and the other end of the pins are soldered into the printed circuit board. The overall length and distance between the pins may be modified to prevent thermal and air flow disturbances from impacting the sensor bead once mounted.

The sensor(s) of the disclosed devices may be configured to generate signals indicative of the composition of the exhaled air. The composition-sensitive sensor(s) may be in addition to the above-described thermistor-based sensors. Alternatively, the composition-sensitive sensor(s) may also be configured to support the spirometric measurements described above, replacing, in some cases, the above-described thermistor(s). The composition-sensitive sensor may have a gas-sensitive coating or film configured to detect a specific gas or gas composition. The composition data may then be used in the risk assessment determinations. For example, the relative amounts of oxygen, carbon dioxide, carbon monoxide, and/or other gases may be used as an indicator of behavioral characteristics of the user profile (e.g., smoking frequency, smoking cessation, etc.). The presence of carbon monoxide may indicate that the user has recently smoked a cigarette despite having entered information via the user interface to the contrary.

The controller 150 may be configured to evaluate the sensor data to validate the test, or determine whether the sensor data is qualified for the spirometric parameter determination. The controller 150 may implement one or more tests for this evaluation. For example, the time elapsed to reach peak flow (from, for example, zero flow) may be determined and evaluated (e.g., in comparison with expected values for a given age, etc.). Alternatively or additionally, the time elapsed from zero flow to ramp-up may be determined and evaluated. The controller 150 may reject the data based on these or other evaluations, and provide an indication to the user via the display 156 as to why the data was rejected. The feedback provided via the display 156 may also include instructions or suggestions for avoiding further data rejection.

The controller 150 may be configured to implement one or more respective risk assessment processes for the respiratory, pulmonary, cardiopulmonary, and cardiovascular diseases. The processes may be based on the association between decreased FEV1 and estimated COPD, heart attack, stroke, and lung cancer. The processes may quantify the user's individual risk of developing the specific disease. The controller 150 may then be configured to present the results in a simplified, easy to understand, yet impactful way that consumers (e.g., non-health professionals) can understand. For example, the display output may be an individual value such as "Your Heart Attack Risk is 21% greater than average." Other display outputs may additionally or alternatively provide current-risk data versus future-risk data based on smoking habits, such as "Your risk of developing COPD in 10 years is currently 33%, or 17% if you quit smoking now". Other display output message for lung function abnormalities may be arranged as a "fuel gauge" design in which the results are indicated on a gauge-like scale with markers for "E", ¼, ½, ¾, and "F" with "E" being zero, ¼ being 25, ½ being 50, ¾ being 75, and "F" being 100% of predicted normal for the FEV1. Yet another output may be a grading scale in which the results are displayed as a grade, i.e., 90-100% of predicted FEV1=A, 80-89% of predicted FEV1=B, 70-79% of predicted=C, 60-69% of predicted FEV1=D, and ≤59% of predicted FEV1=F.

In COPD risk assessments, the output may be based on the following risk factors: age, gender, number of cigarettes smoked daily, and FEV1 percent predicted. In one example, the risk factors may be incorporated into a calculation as follows: relative risk associated with COPD increases 2.5 times with every 10-year increase in age, 2 times for every pack of cigarettes smoked daily, and proportionally for every 10% decrease in FEV1. The above-described processor may be configured to determine the output given these parameters and the FEV1 measurement. Each parameter need not be proportional or linear, but instead one or more of the parameters may be piecewise linear or non-linear. The parameters may vary for a given risk assessment type, and the values of the parameters may vary given new studies or other empirical data for a specific disease. The calculations for non-COPD risk assessments may be based on risk factor data such as smokers with a reduced FEV1 carry a five to six fold risk of lung cancer, and a three to four fold greater risk of cardiovascular mortality.

In one example of a COPD risk assessment device, risk assessments may include factors such as age, gender, number of cigarettes smoked daily, FEV1 percent predicted, and current smoking behavior, but may include more or less factors. A risk assessment model may be generated relating the risk factors to the risk. For example, a curve fitting procedure may be used to generate the model. In some cases, the models are linear combinations of the risk factors. The models may alternatively or additionally include power relations, or polynomial combinations, etc. Different models may be used based on gender, or the model may include one or more adjustment factors to take into account gender. The models may include a number of weights, each weight being associated with a respective risk factor, to fit the experimental data based on the risk factors. For example, one model may be of the form: risk=constant+a*factor1+b*factor2+ c*factor3+ etc. In one example, the risk factors may be incorporated into a model as follows: Approximate relative risk associated with COPD in men increases 2.5 times (weight a) with every 10-year increase in age, 2 times (weight b) for every increased pack of cigarettes smoked daily, and approximate relative risk decreases 30% (weight c) for every 10% increase in FEV1 percent predicted. The above-described processor may be configured to determine the output given these model parameters and the FEV1 measurement.

Each parameter in the risk assessment models need not be proportional or linear. For example, one or more of the parameters in the model may be piecewise linear or non-linear. The parameters may vary for a given risk assessment type, and the values of the parameters may vary given new empirical data for a specific disease.

Models for non-COPD risk assessments may be based on risk factor data such as smokers with a reduced FEV1 carry a five to six fold risk of lung cancer, and a three to four fold greater risk of cardiovascular mortality.

FIG. 9 shows an embodiment directed to providing information regarding lung age. Smoking effectively ages the lungs. The lungs of a smoker deteriorate more rapidly, as if the lungs are aging faster. Unfortunately, the damage caused by smoking is irreversible. Smoking cessation may not allow the lungs to return to normal, but reduction in function may then resume at a normal rate. Smoking cessation may halt the accelerated decline. The embodiment of FIG. 9 recognizes these aspects of lung function in providing information regarding the lung age gap of the patient based on the spirometric parameter (e.g., FEV1) determined by the device. Presentation of the patient's lung age gap may provide the patient with results that improve despite the irreversibility of the damage. Thus, in this embodiment, the output provided by the device may include and provide positive feedback to the user. As the patient gets older, the lung age gap may decline. Such feedback may provide the patient with increased motivation to quit smoking or remain a non-smoker.

The lung age gap may be determined by computing the difference between the user's chronological age and the lung age based on the device measurement, which, in turn, is determinative of a spirometric parameter as described above. For example, a 50 year old smoker with a lung age of 60 has a lung age gap of 10 years. A year later at age 61 the subject tests himself again and because smoking cessation has halted the rapid decline in lung function, he will likely still have a lung age of 60 but his lung age gap is now 9 years, an improvement and positive feedback for this smoker. The lung age gap determination need not be limited to whole numbers or integers. Fractional or other more precise values (e.g., 50.2 years) may provide the user with more frequent opportunities to see improvement.

The size, shape and form factor of the disclosed devices may vary. For example, the disclosed devices need not be bar-shaped. In some cases, the devices may be pen-shaped or pocket-sized. One example of a pen-shaped housing is shown in U.S. Design Pat. No. 541,419, the entire disclosure of which is hereby incorporated by reference.

The risk assessments determined by the disclosed devices need not be based on FEV1. Alternative or additional spirometric parameters may be determined and relied upon to generate a risk assessment, including, for example, forced vital capacity (FVC), forced expiratory volume in six seconds (FEV6), FEV1/FVC, FEV1/FEV6, peak expiratory flow rate (PEFR), etc.

In alternative embodiments, the disclosed devices may include a separable mouthpiece to support use by more than one patient. Such embodiments may be used in health care professional settings such as clinics, physician offices, etc.

Embodiments of the disclosed system and method may be implemented in hardware or software, or a combination of both. Some embodiments may be implemented as computer programs executing on programmable systems comprising at least one processor, a data storage system (including volatile and non-volatile memory and/or storage elements), at least one input device, and at least one output device. Program code may be applied to input data to perform the functions described herein and generate output information. The output information may be applied to one or more output devices, in known fashion. For purposes of this application, a processing system includes any system that has a processor, such as, for example, a digital signal processor (DSP), a microcontroller, an application specific integrated circuit (ASIC), a microprocessor, or a personal computer.

The programs may be implemented in a high level procedural or object oriented programming language to communicate with a processing system. The programs may be configured in software components or modules. The programs may also be implemented in assembly or machine language, if desired. In fact, practice of the disclosed system and method is not limited to any particular programming language. In any case, the language may be a compiled or interpreted language.

The programs may be stored on a storage media or device (e.g., floppy disk drive, read only memory (ROM), CD-ROM device, flash memory device, digital versatile disk (DVD), or other storage device) readable by a general or special purpose programmable processing system, for configuring and operating the processing system when the storage media or device is read by the processing system to perform the procedures described herein. Embodiments of the disclosed system and method may also be considered to be implemented as a machine-readable storage medium, configured for use with a processing system, where the storage medium so configured causes the processing system to operate in a specific and predefined manner to perform the functions described herein.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A health risk assessment device comprising:
a mouthpiece;
a flow path in fluid communication with the mouthpiece;
a sensor disposed in the flow path and configured to generate a signal representative of a dynamically changing air flow in the flow path provided by a user through the mouthpiece;
a user interface configured to allow the user to provide an age of the user; and
a processor coupled to the sensor and configured to:
digitally filter the signal representative of the dynamically changing air flow to generate flow data for the dynamically changing air flow;
implement a test to evaluate the flow data, the test determining time elapsed to reach peak flow;
evaluate the flow data to validate that the dynamically changing air flow is qualified for spirometric parametric determination based on the test;
integrate the flow data to determine a volume for the dynamically changing air flow; and
determine spirometric data for the air flow based on the volume;
wherein the processor is further coupled to the user interface and configured to determine an output specifying a lung age gap based on the spirometric data and the age of the user.

2. The health risk assessment device of claim 1, wherein the spirometric data is representative of forced expiratory volume in one second (FEV1).

3. The health risk assessment device of claim 1, wherein the sensor is configured to capture a dynamic measurement of exhaust air velocity in the flow path.

4. The health risk assessment device of claim 1, further comprising a housing in which the flow path is disposed, and wherein the mouthpiece is integrally formed with the housing.

5. The health risk assessment device of claim 1, further comprising a flow chamber in which the sensor is disposed, wherein the mouthpiece and the flow chamber are non-separable from one another.

6. The health risk assessment device of claim 1, wherein the sensor comprises a thermistor.

7. The health risk assessment device of claim 1, wherein:
the user interface is further configured to allow the user to provide user profile data including smoking history data; and
the processor is further configured to determine a further output specifying a risk that the user develops a disease based on the spirometric data and the smoking history data.

8. A health risk assessment device comprising:
a mouthpiece;
a flow path in fluid communication with the mouthpiece;
a sensor disposed in the flow path and configured to generate a signal representative of a dynamically changing air flow in the flow path provided by a user through the mouthpiece;
a user interface configured to allow the user to provide user profile data including smoking history data and an age of the user; and
a processor coupled to the sensor and configured to:
digitally filter the signal representative of the dynamically changing air flow to generate flow data for the dynamically changing air flow;
implement a test to evaluate the flow data, the test determining time elapsed from zero flow to ramp-up;
evaluate the flow data to validate that the dynamically changing air flow is qualified for spirometric parametric determination based on the test;
integrate the flow data to determine a volume for the dynamically changing air flow; and
determine spirometric data for the air flow based on the volume;
wherein the processor is further coupled to the user interface and configured to determine a plurality of outputs based on the spirometric data and the user profile data and specifying a plurality of health risks of the user, respectively, the plurality of health risks comprising a first health risk for which the respective output specifies a lung age gap, and a second health risk for which the respective output specifies a likelihood that the user develops chronic obstructive pulmonary disease (COPD).

9. The health risk assessment device of claim 8, further comprising a housing in which the flow path is disposed, and wherein the mouthpiece, the sensor, and the housing are non-separable from one another.

10. The health risk assessment device of claim 8, further comprising a flow chamber in which the sensor is disposed, wherein the mouthpiece and the flow chamber are non-separable from one another.

11. The health risk assessment device of claim 8, wherein the sensor is configured to capture a dynamic measurement of exhaust air velocity in the flow path.

12. The health risk assessment device of claim 8, wherein the sensor comprises a thermistor.

13. The health risk assessment device of claim 12, further comprising an air shield disposed along the flow path and configured to shield the thermistor from heat loss arising from air moving in one direction.

14. The health risk assessment device of claim 12, wherein the processor is configured to determine a velocity of the air flow based on a measurement of power provided to the thermistor to maintain the thermistor at a constant temperature.

15. The health risk assessment device of claim 12, wherein the thermistor is configured for operation at a temperature level at which the thermistor is insensitive to barometric and humidity variations.

16. The health risk assessment device of claim 8, wherein the flow path has differing inhalation and exhalation flow resistances.

17. The health risk assessment device of claim 8, wherein the sensor has a single-thermistor architecture.

18. The health risk assessment device of claim 8, wherein the processor is configured to implement an anti-aliasing decimation filter.

19. The health risk assessment device of claim 18, wherein the anti-aliasing decimation filter introduces zero phase shift.

20. The health risk assessment device of claim 8, further comprising an analog pre-filter coupled to the processor.

21. A health risk assessment device comprising:
a mouthpiece;
a housing inseparably attached to the mouthpiece;
a flow path disposed in the housing and in fluid communication with the mouthpiece;
a sensor disposed in the flow path and configured to generate a signal representative of a dynamically changing air flow in the flow path provided by a user through the mouthpiece;
a user interface configured to allow the user to provide user profile data; and
a processor coupled to the sensor and configured to:
digitally filter the signal representative of the dynamically changing air flow to generate flow data for the dynamically changing air flow;
implement a test to evaluate the flow data, the test determining time elapsed to reach peak flow;
evaluate the flow data to validate that the dynamically changing air flow is qualified for spirometric parametric determination based on the test;
integrate the flow data to determine a volume for the dynamically changing air flow; and
determine spirometric data for the air flow based on the volume;
wherein the processor is further coupled to the user interface and configured to determine an output specifying a lung age gap based on the spirometric data and the user profile data; and
wherein the sensor comprises a thermistor.

22. The health risk assessment device of claim 11, wherein the sensor is configured to capture a dynamic measurement of exhaust air velocity in the flow path.

23. The health risk assessment device of claim 11, wherein the housing and the mouthpiece are integrally formed.

24. The health risk assessment device of claim 11, further comprising a flow chamber in which the sensor is disposed, wherein the mouthpiece and the flow chamber are non-separable from one another.

25. The health risk assessment device of claim 11, wherein the sensor has a single-thermistor architecture.

26. The health risk assessment device of claim 11, wherein the flow path has differing inhalation and exhalation flow resistances.

27. The health risk assessment device of claim 11, further comprising an air shield disposed along the flow path and configured to shield the thermistor from heat loss arising from air moving in one direction.

28. The health risk assessment device of claim 11, wherein the processor is configured to determine a velocity of the air flow based on a measurement of power provided to the thermistor to maintain the thermistor at a constant temperature.

29. The health risk assessment device of claim 11, wherein the thermistor is configured for operation at a temperature level at which the thermistor is insensitive to barometric and humidity variations.

30. The health risk assessment device of claim 11, wherein the thermistor is configured as a small-size thermistor.

31. The health risk assessment device of claim 1, wherein the processor is further configured to reject sensor data based on whether the representation fails the test, and provide an indication via the user interface as to why the data was rejected.

32. The health risk assessment device of claim 18, wherein the processor is further configured to reject sensor data based on whether the representation fails the test, and provide an indication via the user interface as to why the data was rejected.

33. The health risk assessment device of claim 21, wherein the processor is further configured to reject sensor data based on whether the representation fails the test, and provide an indication via the user interface as to why the data was rejected.

* * * * *

UNITED STATES PATENT AND TRADEMARK OFFICE
CERTIFICATE OF CORRECTION

PATENT NO. : 9,861,299 B1
APPLICATION NO. : 13/209316
DATED : January 9, 2018
INVENTOR(S) : William Jones, Scott Jones and Louis J. Heeb It is certified that error appears in the above-identified patent and that said Letters Patent is hereby corrected as shown below:

In the Claims

Claim 23, Line 1:
Please remove "11" and replace with --21--.

Claim 32, Line 1:
Please remove "18" and replace with --8--.

Signed and Sealed this
Seventeenth Day of April, 2018

Andrei Iancu
*Director of the United States Patent and Trademark Office*